US006582732B1

(12) United States Patent
Bender et al.

(10) Patent No.: US 6,582,732 B1
(45) Date of Patent: Jun. 24, 2003

(54) SYNERGISTIC COMBINATION OF INSECTICIDES TO PROTECT WOOD AND WOOD-BASED PRODUCTS FROM INSECT DAMAGE

(75) Inventors: Raymond Bender, Gibsonia, PA (US); Alan S. Ross, Pittsburgh, PA (US); Hans A. Ward, Wexford, PA (US)

(73) Assignee: Kop-Coat, Inc., Pittsburgh, PA (US)

( * ) Notice: Subject to any disclaimer, the term of this patent is extended or adjusted under 35 U.S.C. 154(b) by 75 days.

(21) Appl. No.: 09/638,594

(22) Filed: Aug. 15, 2000

(51) Int. Cl.[7] .................. A01N 55/00; A01N 55/08; A01N 59/14; A01N 59/16; A01N 53/02
(52) U.S. Cl. ............... 424/641; 424/617; 424/630; 424/657; 424/658; 424/659; 424/660; 424/DIG. 11; 514/64; 514/461; 514/520; 514/521; 514/531
(58) Field of Search .................. 424/617, 630, 424/641, 657–660, DIG. 11; 514/64, 461, 521, 520, 531

(56) References Cited

U.S. PATENT DOCUMENTS

| 5,207,823 A | * | 5/1993 | Shiozawa ............... 106/18.13 |
| 5,334,585 A | * | 8/1994 | Derian et al. ............... 514/74 |
| 5,346,699 A | * | 9/1994 | Tiernan et al. ............. 424/405 |
| 5,480,638 A |   | 1/1996 | Erwin |
| 5,516,520 A |   | 5/1996 | Yang et al. |
| 5,575,996 A |   | 11/1996 | Erwin |
| 5,880,142 A |   | 3/1999 | Otsu et al. |
| 5,916,356 A |   | 6/1999 | Williams et al. |

FOREIGN PATENT DOCUMENTS

JP          4-241903     *   8/1992

OTHER PUBLICATIONS

Chemical Abstracts 131:55077j, Aug. 1999.*
Van Nostrand Reinhold Encyclopedia of Chemistry, Van Nostrand Reinhold Co., New York, 1984, pp. 1016–1017.*
WPIDS Abstract, accession No. 1992–336830, abstracting JP 4–241903 (Aug. 1992).*
JAPIO Abstract, accession No. 1992–241903, abstracting JP 4–241903 (Aug. 1992).*

* cited by examiner

Primary Examiner—John Pak
(74) Attorney, Agent, or Firm—Debra Z. Anderson; Eckert Seamans Cherin & Mellott, LLC

(57) ABSTRACT

A wood treatment material having a synergistic combination of insecticides including boron-containing compounds and synthetic pyrethroids, is provided. This combination is shown to be especially effective in providing resistance to insect attack when wood is treated with this combination. Resistance to attack by Formosan termites, in particular, is provided, in a cost-effective manner. Also provided is wood treated by this combination, and a method of treatment for composite wood.

18 Claims, No Drawings

SYNERGISTIC COMBINATION OF INSECTICIDES TO PROTECT WOOD AND WOOD-BASED PRODUCTS FROM INSECT DAMAGE

BACKGROUND OF THE INVENTION

1. Field of the Invention

This invention relates to a synergistic combination of two insecticides, boron-containing compounds and synthetic pyrethroids, which when used in combination, give a synergistic result in providing improved resistance to insect attack on wood treated with this combination. Wood treated with this combination, and a method of treating wood, is also included in the present invention.

2. Description of the Prior Art

Wood and wood-based materials, including cellulosic composites and plastic-wood composites, are susceptible to damage from insect pests including ants, beetles and termites.

A particular species of termite, the Formosan subterranean termite, *Coptotermes formosanus* Shiraki, is of particular concern. This termite species is the most widely distributed and damaging termite pest in tropical and subtropical regions of the world and is responsible for tens of millions of dollars each year in costs of damages and control in the State of Hawaii alone. The Formosan termite is an increasingly serious problem across the southern United States as well. The rapid feeding rate, large colony size and aggressive foraging of this termite species make it especially challenging with respect to developing wood treatment substances designed to protect wood and wood products from attack by this particular pest. It is desirable, therefore, to develop treatments which are capable of protecting wood against such an aggressive organism.

Currently, a variety of insecticides, including creosote, chrome-copper-arsenate, organophosphates and boron compounds, are available to protect wood and wood composites against insect attack. Synthetic pyrethroids are also used to protect against pests but are not as economical to use in the amounts needed for sufficient pest control.

U.S. Pat. Nos. 5,480,638 and 5,575,996 disclose a powdered insecticide bait composition comprised of pet food, powdered pyrethrin and boric acid. This patent does not disclose the use of pyrethroids in combination with boron compounds as a wood treatment composition.

U.S. Pat. No. 5,516,620 relates to a controlled release composition in which a insecticide is encapsulated in a starch-borax-urea matrix. This patent does not disclose boron compounds as insecticides or for use in wood treatment products.

U.S. Pat. No. 5,880,142 discloses a composition suitable for controlling termites comprised of a compound of a specific chemical formula used in combination with a pyrethroid. Boron is not disclosed for use as an insecticide.

U.S. Pat. No. 5,916,356 discloses a wood preservative composition comprising a synergistic combination of a biocidal metal compound and a fungicidal compound having a triazole group. The biocidal metal compound can be zinc in the form of an inorganic salt such as zinc borate. This patent does not disclose boron compounds in combination with pyrethroids.

It is desired, therefore, to develop a wood treatment substance capable of protecting wood against extremely aggressive termite attack in an economical manner.

SUMMARY OF THE INVENTION

The present invention fulfills the above need by providing an unusually effective and economical wood treatment that protects wood and wood products against such aggressive termite attack. The present invention provides a unique combination of two classes of insecticides, specifically boron-containing insecticides and synthetic pyrethroids, which in combination provide a more complete resistance to insect attack in a more economical manner, than either compound used alone. A method of treating wood, in particular composite wood materials, with the synergistic combination is included in the present invention, as is the wood treated by this combination.

It is an object of the invention therefore, to provide a combination of insecticides to resist insect attack in wood treated with such substances, in an economical manner.

It is an additional object of the present invention to provide a wood treatment that can protect wood against the extremely aggressive Formosan termite.

It is a further object of the present invention to provide a wood treatment which can resist Formosan termite attack using boron-containing insecticides in combination with synthetic pyrethroids.

These and other objects of the invention will become apparent from the following description and appended claims.

DETAILED DESCRIPTION OF PREFERRED EMBODIMENTS

Accordingly, the present invention provides a wood treatment material comprising a synergistic combination of a boron-containing insecticide and a synthetic pyrethroid. As used herein, the term "wood treatment material" refers to this synergistic combination of insecticides, which may be used with other additives such as resins or solvents, and which is applied to wood by a variety of methods including, but not limited to, spraying, dipping, pressure treating, addition during formation of engineered wood, and other methods known to those skilled in the art that are used to apply such substances to wood.

As used herein, the term "boron-containing insecticide" includes insecticides containing at least one boron compound selected from the group including boron, alkali metal salts of boron, alkaline earth metal salts of boron, metal salts of boron, oxides of boron, boric acid, boric acid esters and salts of these.

It is thought that in respect to the metal salts of boron, that the active part of the compound is the boron, rather than metallic, portion. Preferred boron compounds are the alkali metal, alkaline earth metal or other metal salts of boron. Most preferred is zinc borate.

As used herein, the term "synthetic pyrethroid" includes a group of insect growth regulators that act as neurotoxins and are especially effective against insects that are destructive in the adult stage. This class of insecticides is desirable for pest control because it is considered to be of low toxicity to animals and humans. However, it is preferred to use pyrethroids in combination with other insecticides due to their high cost. Suitable synthetic pyrethroids include deltamethrin, cyfluthrin, permethrin, trilomethrin, cypermethrin, resmethrin and other synthetic pyrethroids. A preferred synthetic pyrethroid is deltamethrin.

As used herein, the term "wood" includes a variety of wood and wood-based materials, including but not limited to logs and other types of dried lumber, green lumber, fiberboards, strand board, laminated veneer lumber, cellulosic composites, plastic wood composites and other types of wood, wood composites and engineered wood formed from wood chips, strands, veneers and adhesives.

On a weight to weight percent basis, the boron-containing compound will be present in the final wood product in an amount of about 0.05 wt. % to about 2.0 wt. %, more preferably about 0.20 wt. % to about 1.0 wt. %. The synthetic pyrethroid will be present in the final wood product in an amount of between about 1 ppm to about 1000 ppm, more preferably between about 5 ppm and about 100 ppm. All weight percent or part-per-million values are based on the total weight of the wood product after treatment.

The insecticides can be applied on the surface of the wood, as in spraying or dipping the wood in a solution containing both insecticides. Other constituents of the solution include a paraffin wax emulsion and water. The insecticides can also be applied to the wood with pressure treatment that is commonly used on solid or engineered wood. A third method, particularly for engineered wood, is to treat the wood chips or strands with the insecticide combination in powder or liquid form prior to formation of the composite wood boards. Wood may be treated by more than one of these methods.

In the third method, the insecticides are combined with wood flakes, chips or strands, a phenolic resin and a water repellant, and fabricated into a wood composite board. This last step may be accomplished in a heated high-pressure press. These severe processing conditions often result in reduced performance of additives such as insecticides. Unexpectedly, the performance of a boron compound in combination with a pyrethroid was not reduced, but was actually improved.

This combination of insecticides has proven to be unusually effective in providing resistance to attack by Formosan termites. It is also expected that the combination will be effective against a variety of other less aggressive pests, including ants, beetles, wasps and other insects.

EXAMPLE

Resistance of five chipboard panels prepared by Kop-Coat, Inc., to attack by the Formosan subterranean termite was evaluated using the no-choice laboratory test specified in the American Wood-Preservers' Association AWPA E1-97 protocol for laboratory evaluation of termite resistance. In this protocol, a test wafer is exposed to 400 Formosan subterranean termites for 4 weeks (28 days). Termites are freshly collected from field locations immediately before the test, and then kept under warm and humid conditions ideal for survival and feeding. This no-choice test represents a worst-case scenario in which termites have no option but to either eat the test wafer, or die from starvation. Typically, untreated Douglas-fir or Southern Yellow Pine wafers are virtually destroyed in the 4-week test period. At the conclusion of the test period, the wafers are visually rated according to the AWPA rating scale of 10, 9, 7, 4, or 0, where a rating of "10" indicates no attack (except for minor surface scratches), and "0" is complete failure of the test wafer. Also recorded is the oven dry weight change of the test wafers, and termite mortality.

Chipboard wafers 1×1×⅜-inch (25×25×10-cm) were cut from panels prepared by Kop-Coat, Inc. (Pittsburgh, Pa.). In addition to five different chipboard panels (9-1, 9-2, 11-1, 12-1, 13-1), Douglas-fir wafers (1×1×¼-inch) were also included as susceptible controls. Evaluations were performed at the University of Hawaii against the Formosan subterranean termite (*Coptotermes formosanus* Shiraki), using the no-choice feeding test protocol recited in AWPA E1-97 (AWPA 1998). The amount of each insecticide used in the panels is as recited in Table 1. All amounts shown are on a weight percent or part-per-million basis where the total weight is the weight of the wood, including resin and wax. Timbertreat DM-5 is a trade designation for deltamethrin.

TABLE 1

| Panel Number | Amount Zinc Borate | Amount Timbertreat DM-5 (ppm) |
| --- | --- | --- |
| 9-1 | 0 | 0 |
| 9-2 | 0.7% (7,000 ppm) | 0 |
| 11-1 | 0.23% (23,000 ppm) | 10 |
| 12-1 | 0.46% (46,000 ppm) | 10 |
| 13-1 | 0 | 100 |

Wafers were oven dried (90° C., 24 hours) to obtain dry weights prior to termite exposure. A single dry wafer was placed on a square of aluminum foil (to minimize any leaching) on the surface of 150 g of damp silica sand (moistened with 30 ml distilled water) inside a screw-top jar (8 cm diameter, 10 cm high). Formosan subterranean termites, *Coptotermes formosanus* Shiraki, were collected from an active field colony immediately before the laboratory test using a trapping technique (Tamashiro et al. 1973). 400 termites (360 workers and 40 soldiers, to approximate natural caste proportions in field colonies) were added to each test jar. Each treatment was replicated 5 times. Also included were 3 additional wafers of each material as "ambient controls"—exposed to the same test conditions as the other wafers, but without addition of any termites to the jar—in order to recognize any weight change in the wafers due to leaching or any other factors unrelated to termite attack.

After adding termites, the jars were placed in an unlighted controlled-temperature cabinet at 28° C. for 4 weeks (28 days), as specified in AWPA E1-97. Each jar was inspected weekly for evidence of termite activity in the soil and on the test materials. At the conclusion of the 4-week test period, percentage termite mortality was recorded, the wafers were rated visually according to the AWPA 0–10 scale (where 10 is sound, 9 is light attack, 7 is moderate attack and penetration, 4 is heavy attack, and 0 is failure of the wood sample), and the oven dry weight change was recorded for each wafer.

RESULTS

Termites continued to be very active on the Douglas-fir controls and on panel 9-1 throughout the 4-week test period. However, termite activity was noted to have decreased on panel 13-1 by the second week of the test (as evidenced by visible "flattening" of the abdomens, slower movement, and fewer termites present upon the test material), and progressively decreasing on panels 12-1, 11-1, and 9-2 as well during the third and fourth weeks.

TABLE 2

| Treatment | Mean Wt. Loss (mg) | Mean Wt. Loss (%) | Mean Mortality (%) |
| --- | --- | --- | --- |
| Panel 9-1 | 1282.80 | 34.18 | 14.70 |
| Panel 9-2 | 239.84 | 6.27 | 97.45 |
| Panel 11-1 | 175.30 | 4.35 | 41.50 |
| Panel 12-1 | 152.36 | 3.99 | 41.45 |

TABLE 2-continued

| Treatment | Mean Wt. Loss (mg) | Mean Wt. Loss (%) | Mean Mortality (%) |
| --- | --- | --- | --- |
| Panel 13-1 | 124.94 | 3.09 | 50.80 |
| Douglas Fir | 1050.26 | 62.73 | 15.95 |

As indicated in Table 2, the Douglas-fir control wafers were virtually destroyed during the 4-week exposure (visual rating of 0, weight loss of 1050 mg or 62.73%). Equivalent destructive feeding was noted on panel 9-1 (visual rating of 0, weight loss of 1283 mg or 34.18%), due to the greater weight of the panel samples in comparison to the Douglas-fir. Termite feeding was progressively less on each of the four remaining panels: panel 9-2 (mean rating of 7.8, mass loss of 6.27%), panel 11-1 (mean rating of 8.6, mass loss of 4.35%) panel 12-1 (mean rating of 8.2, mass loss of 3.99), panel 13-1 (mean rating of 9.8, mass loss of 3.09%).

Termite mortality during the test was low and, again, equivalent on the Douglas-fir controls and on panel 9-1. Interestingly, although feeding damage was greater on panel 9-2 than on the three higher-numbered panels, termite mortality was actually higher (97% vs. 41–50%). It is probable that the higher numbered panels (11-1, 12-1, 13-1) contained high enough levels of active ingredients to deter termite feeding. Thus, termites exposed to these panels ate less than those exposed to panel 9-2, and ingested less of the toxic ingredients. If 9-2 contained a lesser concentration of these active ingredients, it may not have been deterrent to any great extent, and the greater amount of termite feeding that occurred led to ingestion of a larger quantity of the toxic ingredients and thus greater termite mortality. However, with a wood product, the goal is to minimize termite feeding as much as possible, so a low weight loss is in this case more desirable than high termite mortality.

While particular embodiments of this invention have been described above for purposes of illustration, it will be evident to those skilled in the art that numerous variations of the details of the present invention may be made without departing from the invention as defined in the appended claims.

What is claimed is:

1. An insecticide treated wood comprising wood treated with a wood treatment material comprising a synergistic combination of a boron-containing insecticide and a synthetic pyrethroid selected from the group consisting of deltamethrin, permethrin, cyfluthrin, trilomethrin, cypermethrin and resmethrin, said boron-containing insecticide and said synthetic pyrethroid present in sufficient amounts in the wood treatment material so that wood treated with the wood treatment material contains said boron-containing insecticide in an amount of about 0.05 to 2.0 wt % and said synthetic pyrethroid in an amount of about 1 ppm to 1000 ppm, based on the weight of the wood after treatment.

2. The insecticide treated wood of claim 1, wherein the boron-containing insecticide is selected from the group consisting of alkali metal salts of boron, alkaline earth metal salts of boron, metal salts of boron, oxides of boron, boric acid, boric acid esters and salts thereof.

3. The insecticide treated wood of claim 2, wherein the boron-containing insecticide is zinc borate.

4. The insecticide treated wood of claim 2, wherein the boron-containing insecticide is calcium borate.

5. The insecticide treated wood of claim 2, wherein the boron-containing insecticide is sodium borate.

6. The insecticide treated wood of claim 1, wherein the boron-containing insecticide is zinc borate and the synthetic pyrethorid is deltamethrin.

7. The insecticide treated wood of claim 1, wherein the synthetic pyrethroid is deltamethrin.

8. The insecticide treated wood of claim 1, wherein the synthetic pyrethroid is resmethrin.

9. The insecticide treated wood of claim 1, wherein the wood is engineered wood.

10. A method of treating wood comprising treating wood with a wood treatment material comprising a synergistic combination of a boron-containing insecticide and synthetic pyrethroid selected from the group consisting of deltamethrin, permethrin, cyfluthrin, trilomethrin, cypermethrin and resmethrin, said boron-containing insecticide and said synthetic pyrethroid present in sufficient amounts in the wood treatment material so that wood treated with the wood treatment material contains said boron-containing insecticide in an amount of about 0.05 to 2.0 wt % and said synthetic pyrethroid in an amount of about 1 ppm to 1000 ppm, based on the weight of the wood after treatment.

11. The method of claim 10, wherein said method is employed on wood components of an engineered wood product, prior to formation of said engineered wood product.

12. The method of claim 10, wherein the boron-containing insecticide is selected from the group consisting of alkali metal salts of boron, alkaline earth metal salts of boron, metal salts of boron, oxides of boron, boric acid, boric acid esters and salts thereof.

13. The method of claim 12, wherein the boron-containing insecticide is zinc borate.

14. The method of claim 12, wherein the boron-containing insecticide is calcium borate.

15. The method of claim 12, wherein the boron-containing insecticide is sodium borate.

16. The method of claim 10, wherein the boron-containing insecticide is zinc borate and the synthetic pyrethroid is deltamethrin.

17. The method of claim 10, wherein the synthetic pyrethroid is deltamethrin.

18. The method of claim 10, wherein the synthetic pyrethroid is resmethrin.

* * * * *